US011609425B2

(12) United States Patent
Ahn (10) Patent No.: US 11,609,425 B2
(45) Date of Patent: Mar. 21, 2023

(54) AUGMENTED REALITY GLASSES WITH AUTO COREGISTRATION OF INVISIBLE FIELD ON VISIBLE REALITY

(71) Applicant: Pukyong National University Industry-University Cooperation Foundation, Busan (KR)

(72) Inventor: Yeh-Chan Ahn, Busan (KR)

(73) Assignee: Pukyong National University Industry-University Cooperation Foundation, Busan (KR)

( * ) Notice: Subject to any disclaimer, the term of this patent is extended or adjusted under 35 U.S.C. 154(b) by 0 days.

(21) Appl. No.: 17/363,652

(22) Filed: Jun. 30, 2021

(65) Prior Publication Data

US 2022/0003992 A1 Jan. 6, 2022

(30) Foreign Application Priority Data

Jul. 1, 2020 (KR) .................... 10-2020-0080871

(51) Int. Cl.
*G02B 27/00* (2006.01)
*G02B 27/01* (2006.01)
*G06T 19/00* (2011.01)

(52) U.S. Cl.
CPC ....... *G02B 27/0093* (2013.01); *G02B 27/017* (2013.01); *G06T 19/006* (2013.01); *G02B 2027/0178* (2013.01)

(58) Field of Classification Search
CPC .............. G02B 27/0093; G02B 27/017; G02B 2027/0178; G02B 2027/0138; G02B 2027/0187; G02B 27/0172; G02B 27/0189; G02B 27/023; G06T 19/006; A61B 5/7445; A61B 5/745; A61B 5/0059; A61B 2017/00216; A61B 2090/365; A61B 2090/372; A61B 2090/373; A61B 2090/502; A61B 2505/05; A61B 90/36; A61B 34/20; A61B 2034/2055

See application file for complete search history.

(56) References Cited

U.S. PATENT DOCUMENTS

2020/0008899 A1* 1/2020 Tripathi ................ A61B 90/20
2020/0159030 A1 5/2020 Ayres et al.

FOREIGN PATENT DOCUMENTS

| JP | 2016134668 A | 7/2016 |
| JP | 2016521480 A | 7/2016 |
| KR | 1020170042332 A | 4/2017 |
| KR | 1020190102060 A | 9/2019 |
| KR | 1020190133229 A | 12/2019 |

OTHER PUBLICATIONS

An Office Action mailed by the Korean Intellectual Property Office dated Sep. 17, 2020, which corresponds to Korean Patent Application No. 10-2020-0080871.
A Notice of Allowance mailed by the Korean Intellectual Property Office dated Nov. 25, 2020, which corresponds to Korean Patent Application No. 10-2020-0080871.

* cited by examiner

*Primary Examiner* — Jeffery A Brier
(74) *Attorney, Agent, or Firm* — Studebaker & Brackett PC (57) ABSTRACT

Augmented reality glasses with auto coregistration of an invisible field on visible reality which allows eyes to recognize a real space and precisely performs coregistration on only diagnosis and treatment information of invisible light, which is emitted from a specific area, to the real space.

25 Claims, 10 Drawing Sheets

AUGMENTED REALITY GLASSES WITH AUTO COREGISTRATION OF INVISIBLE FIELD ON VISIBLE REALITY

CROSS-REFERENCE TO RELATED APPLICATION

This application claims priority to and the benefit of Korean Patent Application No. 10-2020-0080871, filed on Jul. 1, 2020, the disclosure of which is incorporated herein by reference in its entirety.

BACKGROUND

1. Field of the Invention

The present invention relates to augmented reality glasses with auto coregistration of an invisible field on visible reality, and more particularly, to augmented reality glasses with auto coregistration of an invisible field on visible reality, which allows the eye to directly recognize a real space and precisely performs auto coregistration on only diagnosis and treatment information of invisible light, which is emitted from a specific area, to the real space.

In addition, the present invention relates to augmented reality glasses with auto coregistration of an invisible field on visible reality which provide sufficient eye-box expansion and a wide field of view (FOV) and do not cause a problem of a vergence-accommodation conflict (VAC).

2. Discussion of Related Art

Owing to a deep infiltration depth of near-infrared rays into the human body, various medical devices using the principles of fluorescence, transmission, scattering, and absorption are being released. In addition, with the development of advanced photosensitive sensitizers, the advanced photosensitive sensitizers are being applied to photodiagnosis and phototherapy. Among the advanced photosensitive sensitizers, indocyanine green is a widely used as a photoreactive dye which has obtained approval from the US Food and Drug Administration (FDA). The indocyanine green easily absorbs light of a near-infrared light source ranging from 600 nm to 900 nm and emits fluorescent near-infrared light ranging from 750 nm to 950 nm. In fluorescent imaging (or fluorescence detection) equipment using fluorescence of the indocyanine green, in order to prevent overlap between an absorption wavelength range and an emission wavelength range, an excitation filter is installed in front of a light source and an emission filter is installed in front of a camera (or a photodetector). For example, the excitation filter allows excited light to be transmitted only in a range of 20 nm in left and right bands around 780 nm, and the emission filter allows fluorescence emission to be transmitted only in a range of 20 nm in left and right bands around 840 nm. The indocyanine green is injected into the human body by an intravenous injection and deposited on a tumor with more nascent blood vessels than normal tissue. When a fluorescent imaging device equipped with a light source, a camera, an excitation filter, and an emission filter is used, it is possible to image fluorescent light emitted from the tumor so that a position of the tumor can be known in real time.

Since near-infrared rays are light of an invisible wavelength, in medical fields, a near-infrared image is acquired using a camera with sensitivity in the near-infrared rays and diagnosis or monitoring of a treatment process is performed using the acquired near-infrared image. Recently, since complementary metal-oxide semiconductor (CMOS) cameras are inexpensive and, although not the most sensitive, have sensitivity in the near-infrared rays, the CMOS cameras are widely used for near-infrared rays monitoring. There are also expensive near-infrared dedicated cameras such as InGaAs cameras.

However, when such cameras are used, in order to allow a person to recognize near-infrared rays, the near-infrared rays sensed by the cameras should be converted into visible light, which is recognizable by a person, and displayed on a monitor. The above process inevitably has a disadvantage in that, during surgery, a clinician should turn his or her gaze to a monitor and continuously observe the monitor.

Therefore, a device which shows near-infrared rays coaxially with the clinician's gaze and performs auto coregistration on a space from which the near-infrared rays are emitted to an actual surgical space to show as augmented reality is required, and it is expected that the device can be conveniently used during surgery or a surgical procedure. However, the existing augmented and virtual reality glasses do not elaborately perform coregistration on an augmented and virtual reality space to a real space. In addition, in order to solve the above problem, virtual reality glasses are used to recognize a real space using a plurality of cameras and the recognized real space is displayed on the virtual reality glasses. However, since the above solution should rely on the cameras without directly recognizing the real space, there is a great deal of rejection in medical sites in which safety should be secured.

Meanwhile, in augmented and virtual reality glasses, dizziness does not occur when a digital image should be located at a point at which two eyes gaze simultaneously and lens focuses of the eyes should be set at the point. When gazing points of the two eyes do not match the lens focuses thereof, that is, when a vergence distance does not coincide with an accommodation distance, a vergence-accommodation conflict (VAC) occurs and it is difficult to use the augmented and virtual reality glasses for a long period of time. In particular, when surgery is performed in the vicinity of a near-infrared emission area with hands of the clinician, a vergence distance is close to 80 cm or less so that a VAC phenomenon becomes significantly important. Therefore, in the case of the augmented reality glasses in which a digital image is superimposed on a real workspace located within arm's length of a user, it is very important to solve a VAC problem.

In addition, in augmented and virtual reality glasses, a digital image can be seen only when eyeballs are properly located with respect to the augmented and virtual reality glasses. However, when an alignment between the augmented and virtual reality glasses and the eyeballs should be very precise, since the user inevitably is very inconvenienced, this problem should be solved by giving alignment tolerance to some extent at the positions of the eyeballs. That is, even when the augmented and virtual reality glasses and the eyeballs are roughly aligned, an image can be seen due to the alignment tolerance. Giving the alignment tolerance is referred to as an eye-box expansion.

In the augmented and virtual reality glasses, it is also very important to secure a wide field of view (FOV). That is, as a viewing angle becomes larger, a digital image of a wide FOV can be seen. For example, when surgery is performed in the vicinity of the near-infrared emission area with assistance from the augmented reality glasses while an FOV of a digital image indicating the near-infrared emission area is narrow, much inconvenience may be caused during surgery.

SUMMARY OF THE INVENTION

The present invention is directed to augmented reality glasses with auto coregistration of an invisible field on visible reality, which allows eyes to directly recognize a real space and precisely performs coregistration on only diagnosis and treatment information of invisible light, which is emitted from a specific area, to the real space.

In addition, the present invention includes visualizing invisible rays, such as near infrared rays as well as ultraviolet rays, and performing auto coregistration on the visualized rays to a real space. In addition, a medical field is merely one example, and the present invention is applicable in various industries in which invisible light has information and auto coregistration of the information to a real space generated by visible light is required.

According to an aspect of the present invention, there is provided augmented reality glasses with auto coregistration of invisible field on visible reality which include a glasses body worn on a face of a user, an invisible light emission unit installed on one side of the glasses body and configured to emit invisible light toward a target object, an input unit installed on a front surface of the glasses body and configured to input the invisible light emitted from the target object together with visible light to a waveguide, an information processing unit installed on one side of the glasses body and configured to convert invisible light image information received from the input unit into visible light image information which is recognizable by a person, and an image output unit installed on a rear surface of the glasses body and configured to receive the visible light image information processed in the information processing unit and output an image toward two eyeballs of the user through the waveguide based on the received visible light image information.

The augmented reality glasses may further include a focus adjustment unit installed on one side of the glasses body and configured to adjust a point at which gazes of the two eyeballs converge to exactly match a focus of real and augmented reality image information output from the image output unit, and an eyeball tracking unit installed on one side of the glasses body and configured to predict a vergence distance and transmit distance information to the focus adjustment unit.

The input unit may include a first input coupler which is formed in one end portion of the waveguide and on which invisible light is incident, a first output coupler formed to be spaced a predetermined distance from the first input coupler in the other end portion of the waveguide and configured to output the invisible light incident from the first input coupler to a camera, and the camera configured to capture the invisible light output from the first output coupler.

The image output unit may include a display configured to output the visible light image information received from the information processing unit, a second input coupler formed in an end portion of the waveguide and configured to receive the visible light image information output from the display, and a second output coupler formed to be spaced a predetermined distance from the second input coupler in the waveguide and formed to allow information received from the second input coupler to be output to the two eyeballs of a user, wherein the second output coupler may be formed to allow an image output position to correspond to an actual position of the target object.

The display may transmit information included in the invisible light to the second input coupler in the form of visible light using a pseudo color which is contrasted with real image information recognized by the user.

The camera may transmit image information to the information processing unit, and the information processing unit may process the received image information and transmits the processed image information to the display.

The eyeball tracking unit may track a gaze of the eyeball looking at a real space to determine the vergence distance and input determined information to the information processing unit, and the information processing unit may calculate the vergence distance of the eyeball in real time on the basis of input information.

The focus adjustment unit may include a first focus adjustment part formed as a transparent optical system, which may include one or more of a reflective element, a refractive element, a diffractive element, a holographic element, and a polarizing element, and cause refraction of light, and a second focus adjustment part formed as a transparent optical system, which may include one or more of a reflective element, a refractive element, a diffractive element, a holographic element, and a polarizing element, and may cause refraction of light.

The focus adjustment unit may receive vergence distance information measured in the eyeball tracking unit and calculated in the information processing unit in real time, compare a focal length of a digital image including the invisible light information with the vergence distance of the eyeball, and maintain a difference between the focal length and the vergence distance within a diopter value of 0.25.

The first focus adjustment part may be located on left and right sides to correspond to the two eyeballs of the user, and the second focus adjustment part may be located on the left and right sides to correspond to the two eyeballs of the user and formed to allow the image output position to be coregistered to gazes toward the target object.

The image output unit may include a display configured to output the visible light image information received from the information processing unit, a second input coupler formed in an end portion of the waveguide and configured to receive the visible light image information output from the display, and a second output coupler installed to be spaced a predetermined distance from the second input coupler in the waveguide and formed to allow information received from the second input coupler to be output to the two eyeballs of a user, wherein the second output coupler may be formed to allow an image output position to correspond to an actual position of the target object, and each of the first input coupler, the first output coupler, the second input coupler, and the second output coupler may secure a large viewing angle of 80 degrees or more by including and combining one or more of a reflective element, a refractive element, a diffractive element, a holographic element, and a polarizing element.

The first input coupler may be located on each of left and right sides to correspond to the two eyeballs of the user, the first output coupler and the camera may be spaced apart from the first input coupler and located on the left and right sides in the glasses body, the second output coupler may be located on each of the left and right sides to correspond to the two eyeballs of the user, and the display and the second input coupler may be spaced apart from the second output coupler and located on the left and right sides in the glasses body, wherein the second output coupler may be formed to allow an image output position to be coregistered to gazes toward the target object.

Each of the first input coupler and the second output coupler may be any one among a diffractive optical element, a holographic optical element, or a pin mirror.

The first input coupler or the first output coupler may further include a filter on a front surface thereof to allow only the invisible light to be transmitted to the camera.

The waveguide may be formed of a first waveguide and a second waveguide, the first waveguide may include a first input coupler which is formed in one end portion of the first waveguide and on which the invisible light is incident, a first output coupler formed to be spaced a predetermined distance from the first input coupler in the other end portion of the first waveguide and configured to output the invisible light incident from the first input coupler, and a camera configured to capture the invisible light output from the first output coupler, and the second waveguide may include a second input coupler formed in an end portion of the second waveguide and configured to receive image information output from the display, and a second output coupler installed to be spaced a predetermined distance from the second input coupler in the second waveguide and formed to allow information received from the second input coupler to be output to the two eyeballs of a user.

The first input coupler may be any one among a first diffractive optical element, a first holographic optical element, and a first pin mirror which are provided on one side of the first waveguide, and the second input coupler may be any one among a second diffractive optical element, a second holographic optical element, and a second pin mirror which are provided on one side of the second waveguide.

The first input coupler or the first output coupler may further include a first filter on a front surface thereof to allow only the invisible light to be transmitted to the camera.

The invisible light emission unit may include a second filter to allow only invisible light in a specific wavelength range to be emitted toward the target object.

The focus adjustment unit may be formed in a parallel light structure in which a focus adjustment function of solving a vergence-accommodation conflict (VAC) problem may be maintained and, simultaneously, a function of securing a quantity of light and implementing eye-box expansion through entrance pupil expansion and exit pupil expansion may be achieved.

The waveguide may be made of a transparent optical material through which visible light passes, any one among a freeform optical element, a flat optical device, and a curved optical device may be used as the waveguide, and a vision correction function for the user may be added to the waveguide as in ordinary glasses.

Each of the input unit and the image output unit may be formed in a structure having one or more wavelength channels, and the structure may solve chromatic aberration by allowing only a specific wavelength to be transmitted to each of the one or more wavelength channels.

The first focus adjustment part may be formed to exhibit an effect equivalent to a depth of focus of an eyeball lens by acting in combination with a lens installed in the first output coupler, thereby automatically applying a realistic optical blur to the camera.

The eyeball tracking unit may be formed of separate cameras and lighting which correspond to the two eyeballs or may have a structure of a vergence tracker using electrooculographic signals of the two eyeballs.

A shape of each of the first output coupler and the second input coupler may have a birdbath structure.

BRIEF DESCRIPTION OF THE DRAWINGS

The above and other objects, features and advantages of the present invention will become more apparent to those skilled in the art by describing exemplary embodiments thereof in detail with reference to the accompanying drawings, in which.

DETAILED DESCRIPTION OF EXEMPLARY EMBODIMENTS

Hereinafter, augmented reality glasses with auto coregistration of an invisible field on visible reality according to embodiments of the present invention will be described in detail with reference to the accompanying drawings. The present invention may be modified in various forms and may have a variety of embodiments and, therefore, specific embodiments will be illustrated in the drawings and a description thereof will be given in detail in the following description. The embodiments to be disclosed below, therefore, are not to be taken in a sense which limits the present invention to specific embodiments and should be construed to include modification, equivalents, or substitutes within the spirit or technical scope of the present invention. In describing each drawing, a similar reference numeral is assigned to a similar component. In the accompanying drawings, dimensions of structures are shown in an enlarged scale for clarity of the present invention.

Although terms "first," "second," and the like may be used herein to describe various components, these components should not be limited to these terms. The terms are used only for the purpose of distinguishing one component from another component. For example, without departing from the scope of the present invention, a first component may be referred to as a second component, and similarly, a second component may also be referred to as a first component.

Terms used herein are used only for the purpose of describing specific embodiments and are not intended to limit the present specification. Unless the context clearly dictates otherwise, the singular form includes the plural form. It should be understood that the terms "comprise,"

"include," and "have" specify the presence of stated herein features, numbers, steps, operations, components, elements, or combinations thereof but do not preclude the presence or possibility of adding one or more other features, numbers, steps, operations, components, elements, or combinations thereof.

Unless otherwise defined, all terms including technical or scientific terms used herein have the same meaning as commonly understood by those skilled in the art to which the present invention pertains. General terms that are defined in a dictionary shall be construed as having meanings that are consistent in the context of the relevant art and will not be interpreted as having an idealistic or excessively formalistic meaning unless clearly defined in the present invention.

Figure 1:
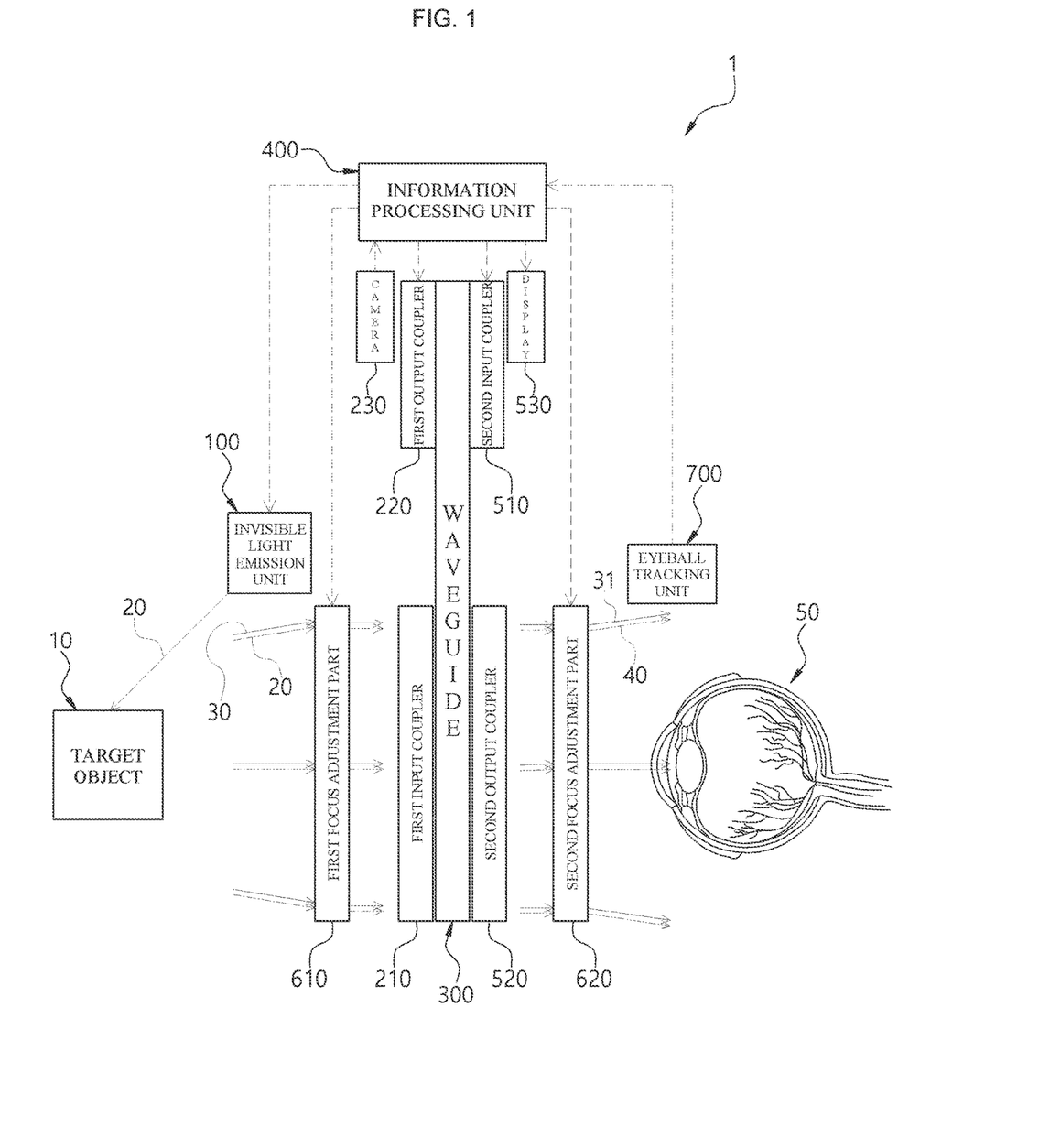
FIGS. 1 and 3 are conceptual diagrams illustrating augmented reality glasses with auto coregistration of an invisible field on visible reality according to a first embodiment of the present invention.
Figure 3:
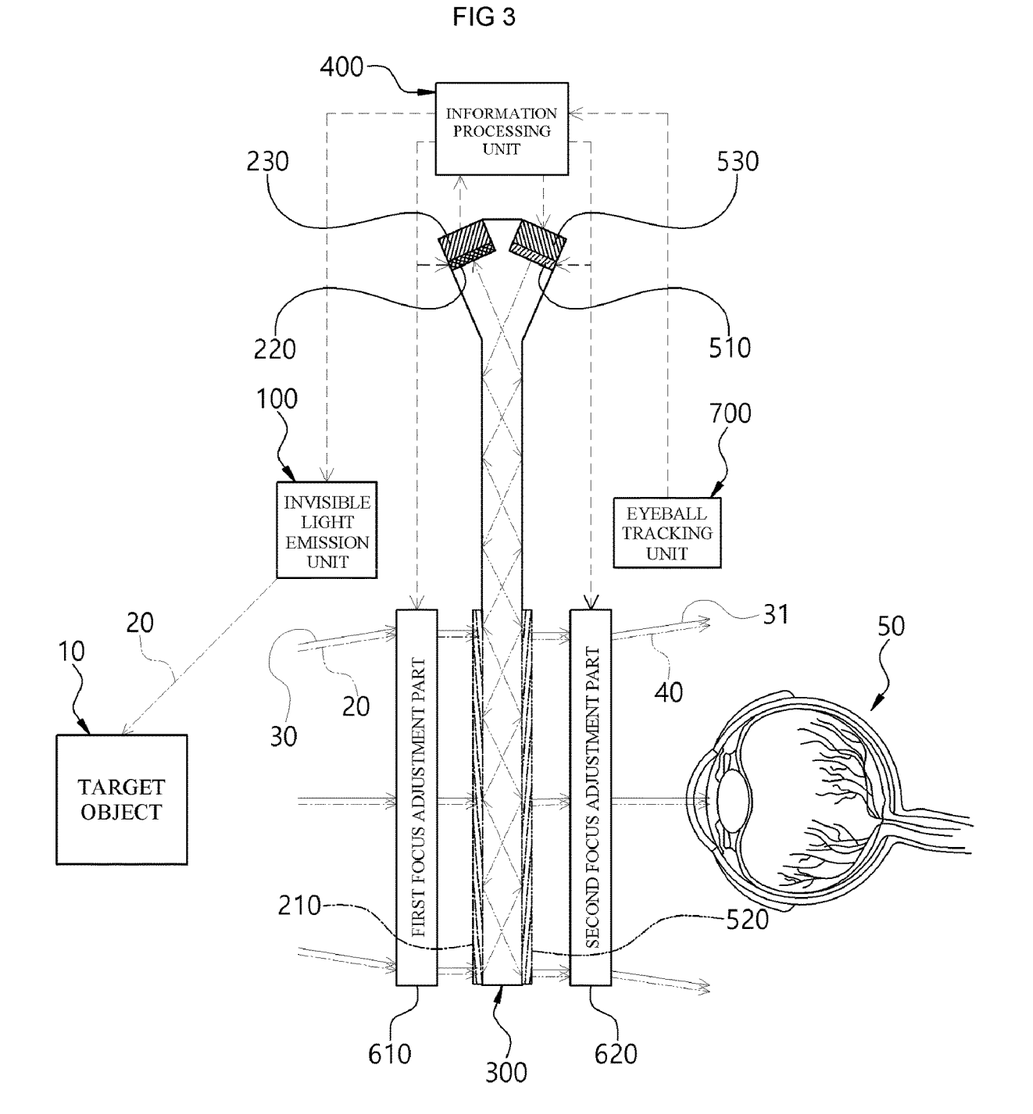

FIGS. 1 and 3 illustrate augmented reality glasses 1 with auto coregistration of an invisible field on visible reality according to a first embodiment of the present invention.

Referring to the drawings, the augmented reality glasses 1 with auto coregistration of invisible field on visible reality include a glasses body, an invisible light emission unit 100, an input unit 200, an information processing unit 400, an image output unit 500, a focus adjustment unit 600, and an eyeball tracking unit 700.

The invisible light emission unit 100 may be installed on one side of the glasses body to emit invisible light 20 toward a target object 10. The invisible light emission unit 100 may be mounted at any one position of the augmented reality glasses 1 or formed in the form of being attached to a part of a head or body of a user through a separate support. Alternatively, the invisible light emission unit 100 may be integrally formed with a lighting device such as an operating light of an operating room or formed in the form of being separately attached to the lighting device. In addition, the invisible light emission unit 100 includes a second filter to emit only invisible light in a specific wavelength range.

The input unit 200 is installed on one side of the glasses body to input invisible light 20 emitted from the target object 10 to a waveguide 300 together with visible light 30 and includes a first input coupler 210, a first output coupler 220, and a camera 230.

The first input coupler 210 is formed in one end portion of the waveguide 300, the invisible light 20 is incident on the first input coupler 210, and the first output coupler 220 is formed to be spaced a predetermined distance from the first input coupler 210 in the other end portion of the waveguide 300 and outputs the invisible light 20 incident from the input coupler 210 to the camera 230.

The first input coupler 210 is a portion in which the invisible light 20 is incident on the waveguide 300, is made of an incident material through which light is incident, and may be formed to be inserted into the waveguide 300 or formed as a separate pattern so as to allow light to be incident on a portion of the waveguide 300.

The first output coupler 220 outputs the invisible light 20 incident from the first input coupler 210 and is formed to be spaced a predetermined distance from the first input coupler 210 on the waveguide 300. Alternatively, the first output coupler 220 may be formed of an incident material, through which light may be output, inserted into the waveguide 300 or formed as a separate pattern so as to allow light to be output to a portion of the waveguide 300.

The camera 230 captures the invisible light 20 output from the first output coupler 220.

The image output unit 500 includes a display 530, a second input coupler 510, and a second output coupler 520.

The display 530 transmits augmented reality information of the invisible light 20 in the form of visible light augmented reality image information 40 using a pseudo color, which may be contrasted with visible light reality image information 31 recognized by the user, to the second input coupler 510.

In the present embodiment, when it is assumed to be the operating room, since colors of organs and blood are red colors, the display 530 outputs blue or green colors as a complementary color to contrast to the red colors so that the visible light reality image information 31 may be distinguished from visible light augmented reality image information 40.

The display 530 may be formed of a micro organic light-emitting diode (OLED) display, a micro LED display, a liquid crystal on silicon (LCoS) display, or an OLED on silicon (OLEDoS) display. The image output unit 500 may be formed in the form of a holographic display or a light field display to solve a VAC problem and an aberration problem (the solution is to exactly adjust focuses of the visible light augmented reality image information 40 output from the image output unit 500 and the visible light reality image information 31 output from the target object 10 to coincide with each other at a position at which gazes of the two eyeballs 50 converge). However, a type of the display 530 is not limited thereto.

The second input coupler 510 is formed in an end portion of the waveguide 300 and receives the visible light augmented reality image information 40 output from the display 530.

The second output coupler 520 is installed to allow the visible light augmented reality image information 40 received from the second input coupler 510 to be output to the eyeball 50 of the user and is formed to be spaced a predetermined distance from the second input coupler 510 in the waveguide 300.

In this case, it is preferable that the second output coupler 520 is formed such that an image output position corresponds to an actual position of the target object 10.

The waveguide 300 is formed of a transparent optical material so as to allow the invisible light 20 to propagate to the first input coupler 210 and the first output coupler 220 and allow the visible light augmented reality image information 40 to propagate between the second input coupler 510 and the second output coupler 520. It is preferable that the waveguide 300 has a very light weight and a thin thickness regardless of a shape such as a parallel plate, a rectangular shape, and a circular shape.

The waveguide 300 may be made of a transparent optical material through which the visible light 30 passes, and a freeform optical element, a planar optical element, or a curved optical element may be used, and like ordinary glasses, a vision correction function of the user may be added to the waveguide 300.

For example, the waveguide 300 may be formed to have a curved surface instead of a flat surface or a freeform lens to correct vision of the user and may be customized according to the user.

Each of the input unit 200 and the image output unit 500 may be formed in a structure having one or more wavelength channels, and only a specific wavelength may be transmitted to each channel to solve chromatic aberration.

The present invention is characterized in that each of the first input coupler 210, the first output coupler 220, the second input coupler 510, and the second output coupler 520 secures a large viewing angle of 80 degrees or more by including and combining one or more of a reflective element, a refractive element, a diffractive element, a holographic element and a polarizing element.

The first input coupler 210 is characterized by having a structure capable of securing a maximal quantity of the invisible light 20 through entrance pupil expansion.

The present invention is characterized in that the second output coupler 520 is capable of first-dimensional and second-dimensional eye-box expansions through exit pupil expansion so that, even when a separation occurs in relative positions of the first input coupler 210 and the second output coupler 520 with respect to the eyeball 50, a stable visual image is provided.

Entrance pupil and exit pupil expansion may be implemented using a parallel light structure in which a focus of the light incident on the first input coupler 210 and a focus of the light output from the second output coupler 520 are located at infinite positions. When the parallel light structure is achieved, it is possible to easily design the input unit 200 including the first input coupler 210 so as to allow light incident in parallel on a large area to be collected at one point of the first output coupler 220. Thus, in the parallel light structure, as a size of an entrance pupil becomes larger, a camera may secure a larger quantity of light. In addition, when the parallel light structure is achieved, it is possible to easily form the image output unit 500 including the second output coupler 520 which converts light from one point of the display 530 into parallel light. Therefore, in the parallel light structure, the eye-box expansion may be easily performed through the exit pupil expansion.

In order to prevent a VAC, the focus adjustment unit 600 may locate a virtual image of a digital augmented reality image in real time using a first focus adjustment part 610 and a second focus adjustment part 620 and maintain the parallel light structure which allows the focus of the light incident on the first input coupler 210 and the focus the light output from the second output coupler 520 to be located at the infinite positions.

The present invention is characterized in that the first focus adjustment part 610 of the focus adjustment unit 600 is installed on a side of the first input coupler 210 toward the target object 10 to a positive focal length, the second focus adjustment part 620 is installed to be spaced a predetermined distance from the first focus adjustment part 610 on a side of the second output coupler 520 toward the eyeball 50 to have a negative focal length, and absolute values of the two focal lengths become equal so that the parallel light structure is maintained and there is no distortion in the real world recognized by the eyeball 50.

Therefore, the parallel light structure is achieved by a method of maintaining a focus adjustment function to solve the VAC problem and, "simultaneously," achieving a function of securing a quantity of light and implementing the eye-box expansion through the entrance pupil expansion and the exit pupil expansion.

In addition, for a user who needs vision correction, the focal length of the second focus adjustment part 620 may be increased or decreased by as much as a diopter value required for the vision correction.

The focus adjustment unit 600 adjusts a point at which gazes of the two eyeballs 50 converge to accurately match the focus of the visible light augmented reality image information 40 output from the image output unit 500 and the focus of the visible light reality image information 31 emitted from the target object 10 and includes the first focus adjustment part 610 and the second focus adjustment part 620.

The first focus adjustment part 610 includes one or more of a reflective element, a refractive element, a diffractive element, a holographic element, and a polarizing element and is preferably located on left and right sides so as to correspond to the two eyeballs 50 of the user.

The present invention is characterized in that, when the first focus adjustment part 610 is formed to exhibit an effect equivalent to a depth of focus of an eyeball lens by acting in combination with a lens installed in the first output coupler 220, the first focus adjustment part 610 may receive information on the invisible light 20 to transmit the information to the first output coupler 220 and automatically endow a realistic optical blur with the digital image, that is, spatial information of the invisible light 20, on the camera 230.

When the eyeball 50 recognizes and looks at an object, the optical blur serves to give a sense of perspective by blurring the surrounding environment. When there is no optical blur, the sense of perspective may disappear, and when the optical blur is excessive, a different feeling may be given.

Thus, in the present invention, since an optical blur in the real space recognized by the eyeball 50 and the optical blur in the digital image are equal to each other, a three-dimensional coregistration image that is coregistered easily may be recognized.

The second focus adjustment part 620 may include one or more of a reflective element, a refractive element, a diffractive element, a holographic element, and a polarizing element, and an image output position is formed to be coregistered on a gaze toward the target object 10.

Each of the first focus adjustment part 610 and the second focus adjustment part 620 may be formed as a transparent optical system, which includes one or more of a reflective element, a refractive element, a diffractive element, a holographic element, and a polarizing element, and causes refraction of light. In order to achieve weight reduction, a variable focus lens such as a plurality of pancharatnam-berry phase (PBP) lenses, a pancake lens, a liquid crystal lens, or a liquid lens may be used, but the present invention is not limited thereto.

The eyeball tracking unit 700 may predict a vergence distance and transmit distance information to the focus adjustment unit 600. In order to serve as a vergence tracker which tracks a gaze of the eyeball 50 looking at the real space and determines a vergence distance, separate cameras and lighting, which correspond to the two eyeballs 50, may be disposed in the eyeball tracking unit 700, or the eyeball tracking unit 700 may use electrooculographic signals of the two eyeballs 50.

Figure 2:
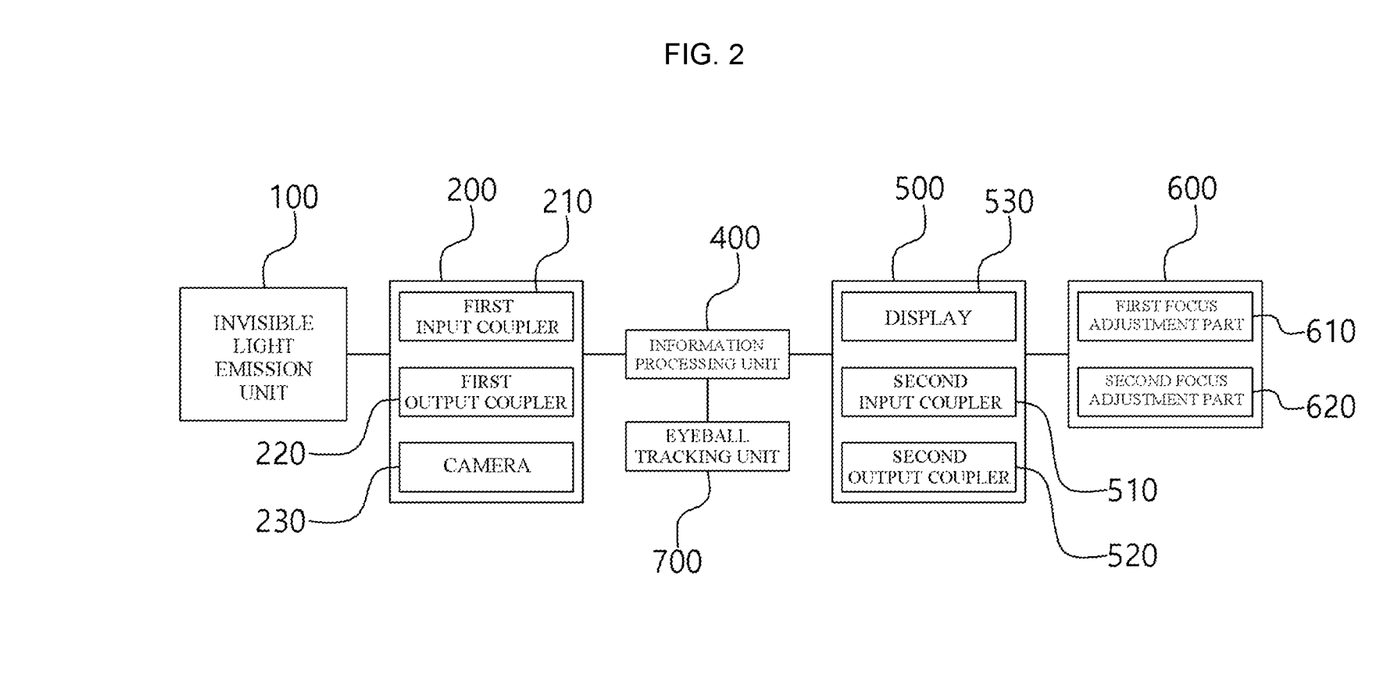
FIG. 2 is a conceptual block diagram illustrating a configuration of the augmented reality glasses with auto coregistration of an invisible field on visible reality according to the first embodiment of the present invention.

The information processing unit 400 transmits signals to the first output coupler 220, the display 530, the first output coupler 220, and the second input coupler 510 and performs adjustment on an aperture value of a lens, a focal point, a frame rate, an exposure time, and International Standard Organization (ISO) sensitivity.

When the first embodiment of the present invention is applied to the two eyeballs 50, first input couplers 210 are located on left and right sides to correspond to the two eyeballs 50 of the user, the first output coupler 220 and the camera 230 are spaced apart from the first input couplers 210 on the left and right sides and located on both sides of the glasses body, second output couplers 520 are located on left and right sides to correspond to the two eyeballs 50 of the user, the display 530 and the second input coupler 510 are spaced apart from the second output couplers 520 on the left and right sides and located on both sides of the glasses body, and the second output couplers 520 may be formed such that the image output position is to be coregistered on the gaze toward the target object 10.

Except for the first input coupler 210, the first output coupler 220, the camera 230, the second input coupler 510, and the second output coupler 520, all remaining components are the same as those described above, and thus detailed descriptions thereof will be omitted herein.

Figure 4:
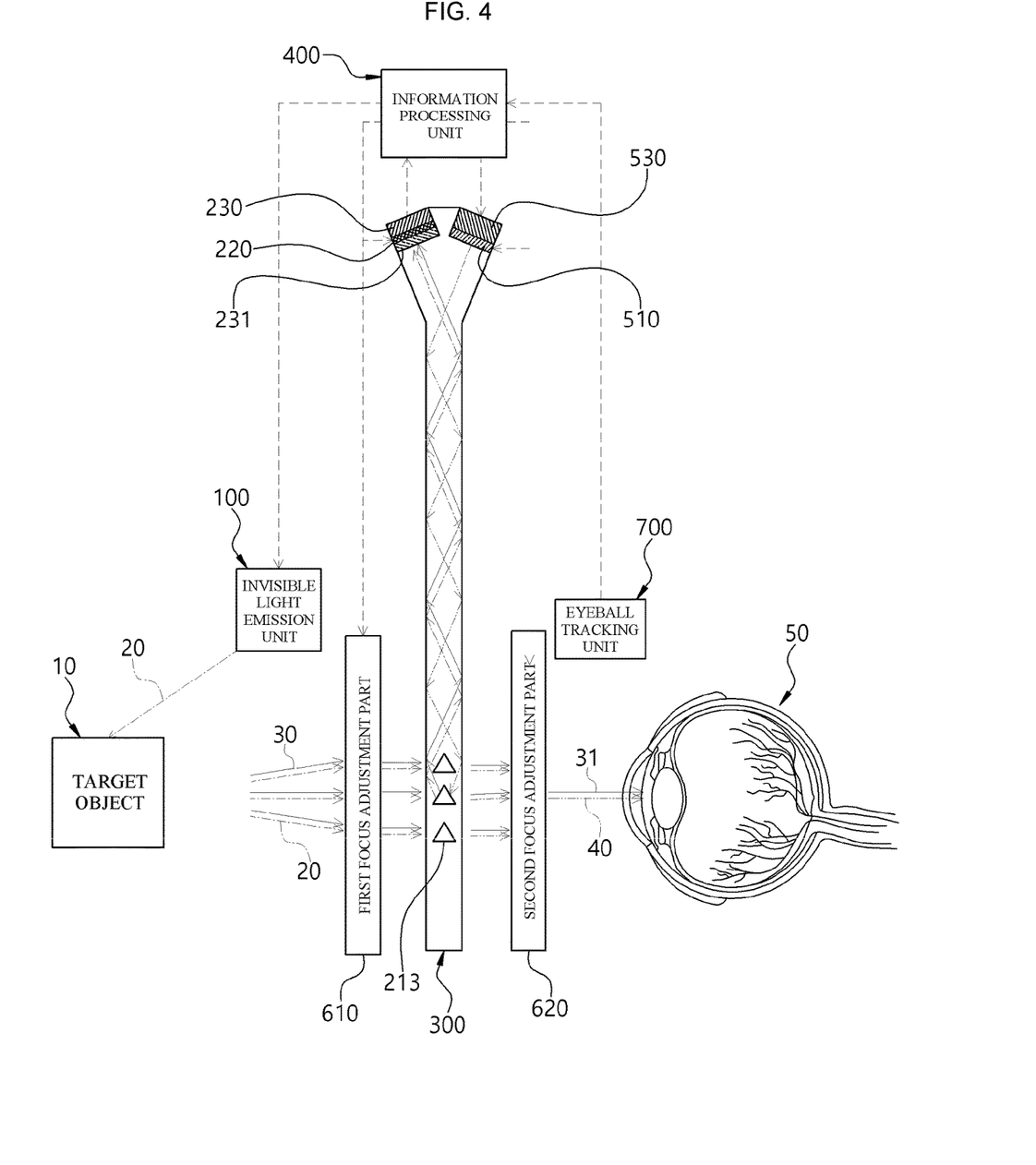
FIG. 4 is a conceptual diagram illustrating augmented reality glasses with auto coregistration of an invisible field on visible reality according to a second embodiment of the present invention.

FIG. 4 illustrates augmented reality glasses 1 with auto coregistration of an invisible field on visible reality according to a second embodiment of the present invention.

In the present embodiment, a first input coupler 210 and a second output coupler 520 are formed of double-sided pin mirrors 213.

Figure 9:
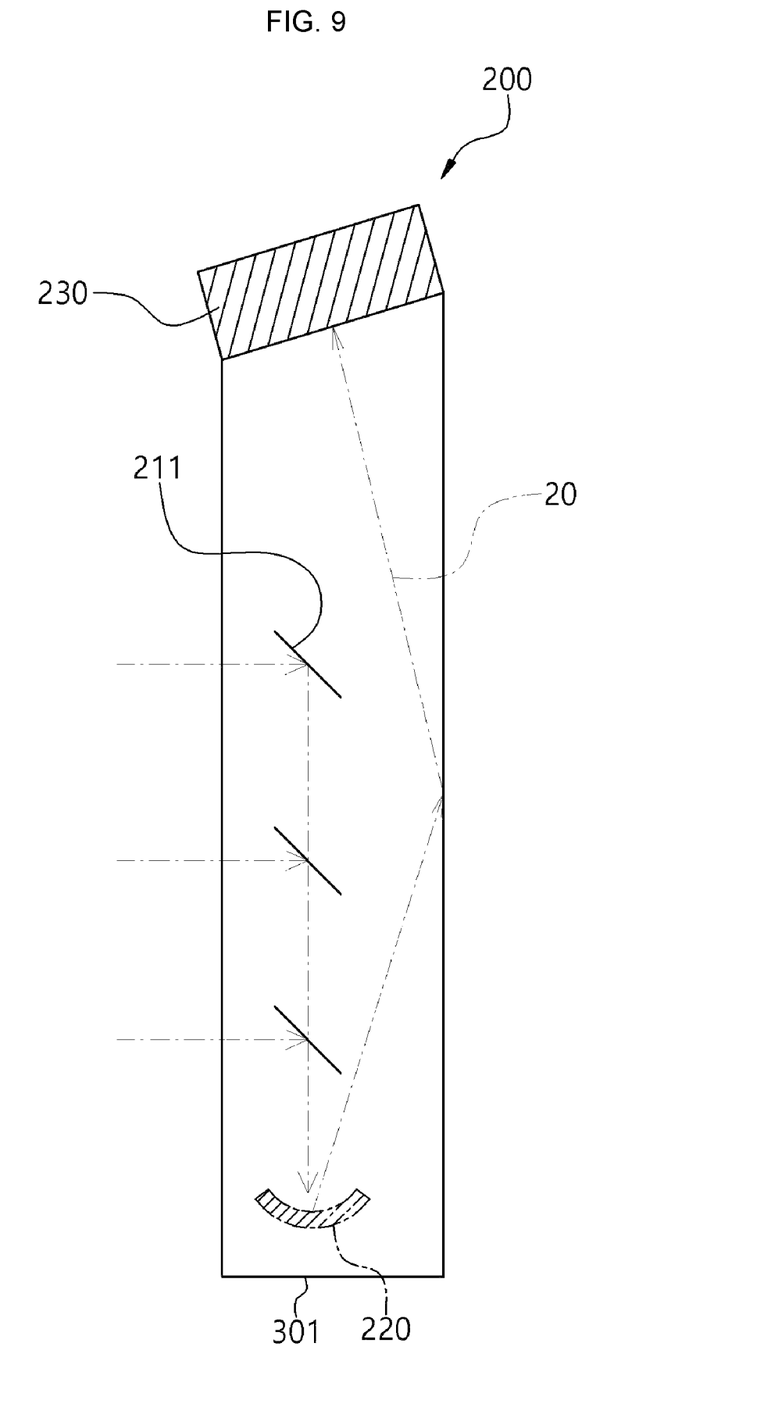
FIG. 9 is a conceptual diagram illustrating a birdbath structure of a first output coupler in FIGS. 1 to 8.
Figure 10:
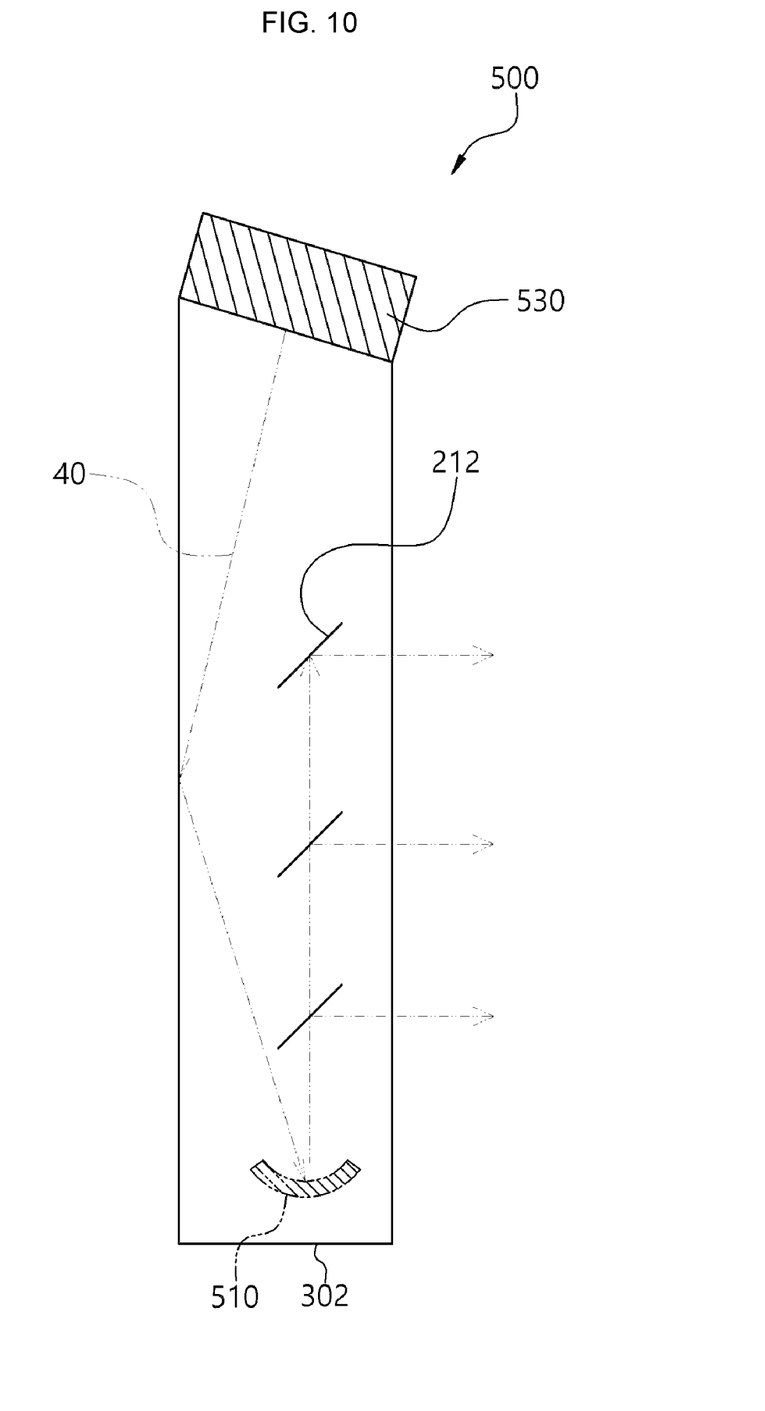
FIG. 10 is a conceptual diagram illustrating a birdbath structure of a second input coupler in FIGS. 1 to 8.

As shown in FIGS. 9 to 10, a first output coupler 220 and a second input coupler 510 need not always be located in front of the camera 230 and the display 530. In some cases, each of the first output coupler 220 and a second input coupler 510 may be located at an end opposite to the waveguide 300 and may have a shape of a birdbath-structured concave mirror.

It is preferable to further include a first filter 231 in the first input coupler 210 or the first output coupler 220 so as to allow only invisible light 20 to be transmitted to the camera 230.

In the present embodiment, except for the first input coupler 210, the first output coupler 220, and the first filter 231 in the waveguide 300, the remaining components are the same as those of the first embodiment, and thus detailed descriptions thereof will be omitted herein.

Figure 5:
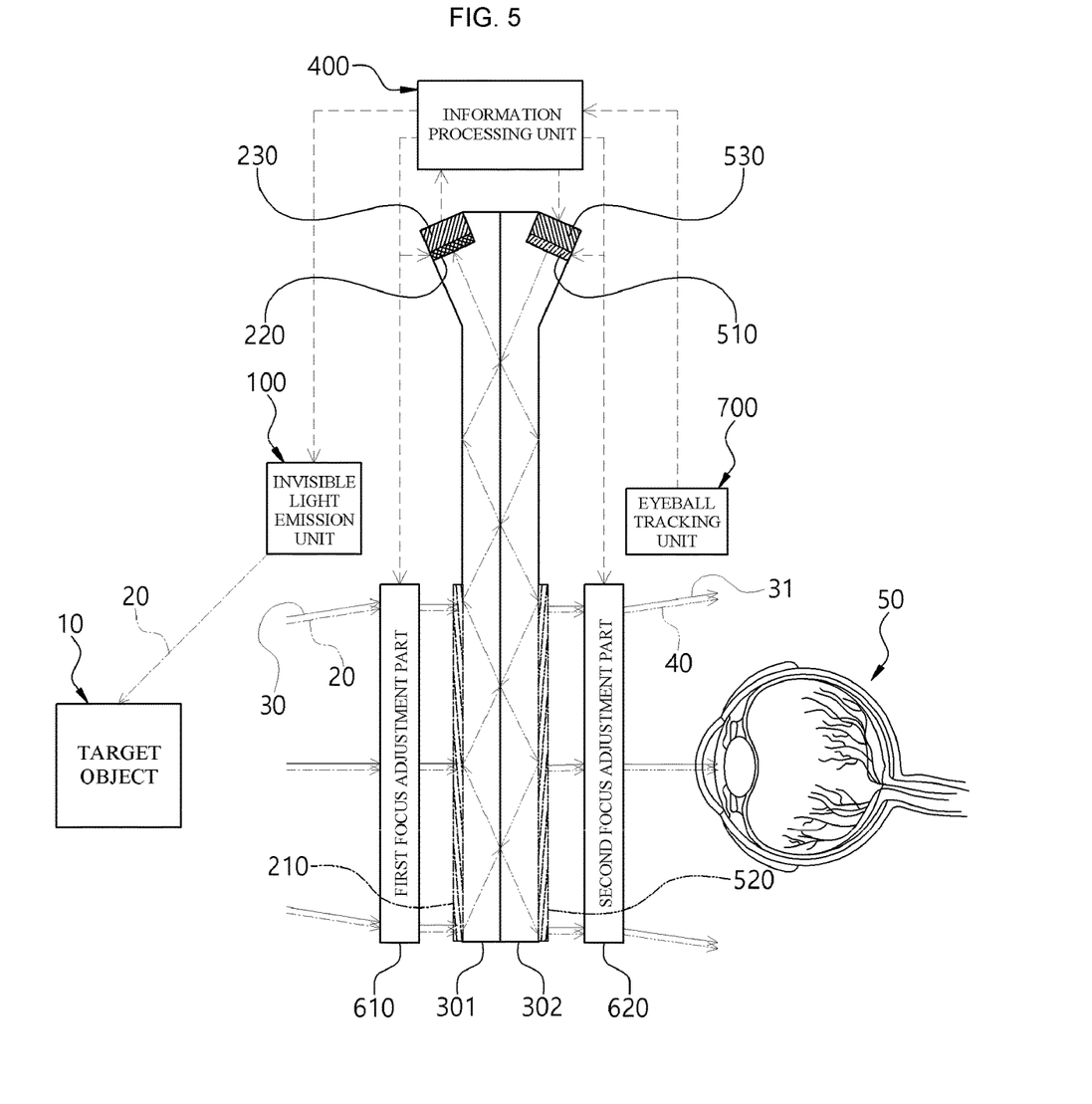
FIG. 5 is a conceptual diagram illustrating augmented reality glasses with auto coregistration of an invisible field on visible reality according to a third embodiment of the present invention.

FIG. 5 illustrates augmented reality glasses 1 with auto coregistration of an invisible field on visible reality according to a third embodiment of the present invention.

A waveguide 300 is formed of a first waveguide 301 and a second waveguide 302. The first waveguide 301 includes a first input coupler 210 which is formed at an end portion of the first waveguide 301 and on which invisible light 20 is incident, and a first output coupler 220 formed to be spaced a predetermined distance from the first input coupler 210 in the first waveguide 301 and configured to output the invisible light 20 incident from the first input coupler 210.

The second waveguide 302 includes a second input coupler 510 formed at an end portion of the second waveguide 302 and configured to receive image information output from the display 530, and a second output coupler 520 formed to be spaced a predetermined distance from the second input coupler 510 in the second waveguide 302 and installed to allow information received from the second input coupler 510 to be output to the eyeball 50 of the user.

In the present embodiment, except for the first waveguide 301 and the second waveguide 302, the remaining components are the same as those of the first embodiment, and thus detailed descriptions thereof will be omitted herein.

Figure 6:
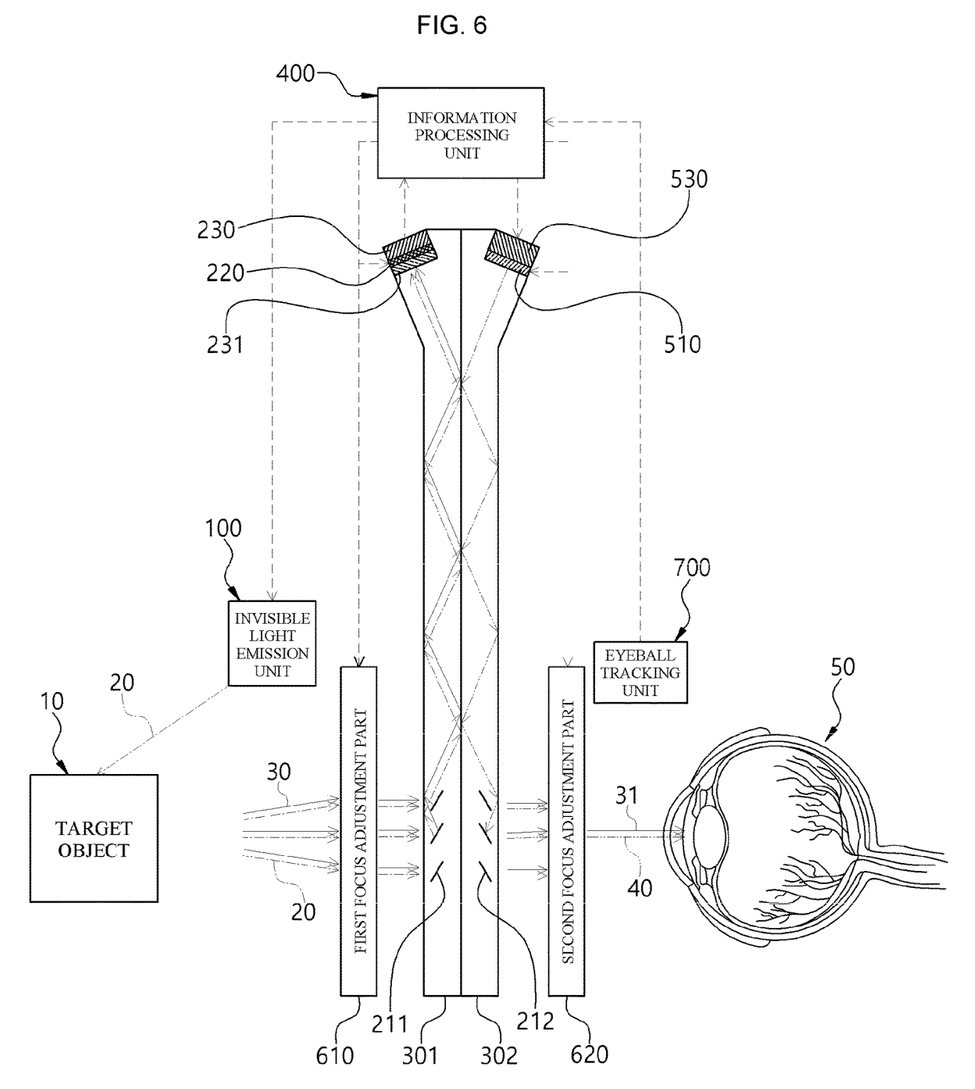
FIG. 6 is a conceptual diagram illustrating augmented reality glasses with auto coregistration of an invisible field on visible reality according to a fourth embodiment of the present invention.

FIG. 6 illustrates augmented reality glasses 1 with auto coregistration of an invisible field on visible reality according to a fourth embodiment of the present invention.

The present invention is characterized in that a first input coupler 210 is a first pin mirror 211 provided on one side of a first waveguide 301, and a second output coupler 520 is a second pin mirror 212 provided on one side of a second waveguide 302.

In the present embodiment, except for the first waveguide 301, the second waveguide 302, the first input coupler 210, and the second output coupler 520, the remaining components are the same as those of the second embodiment, and thus detailed descriptions thereof will be omitted therein.

Figure 7:
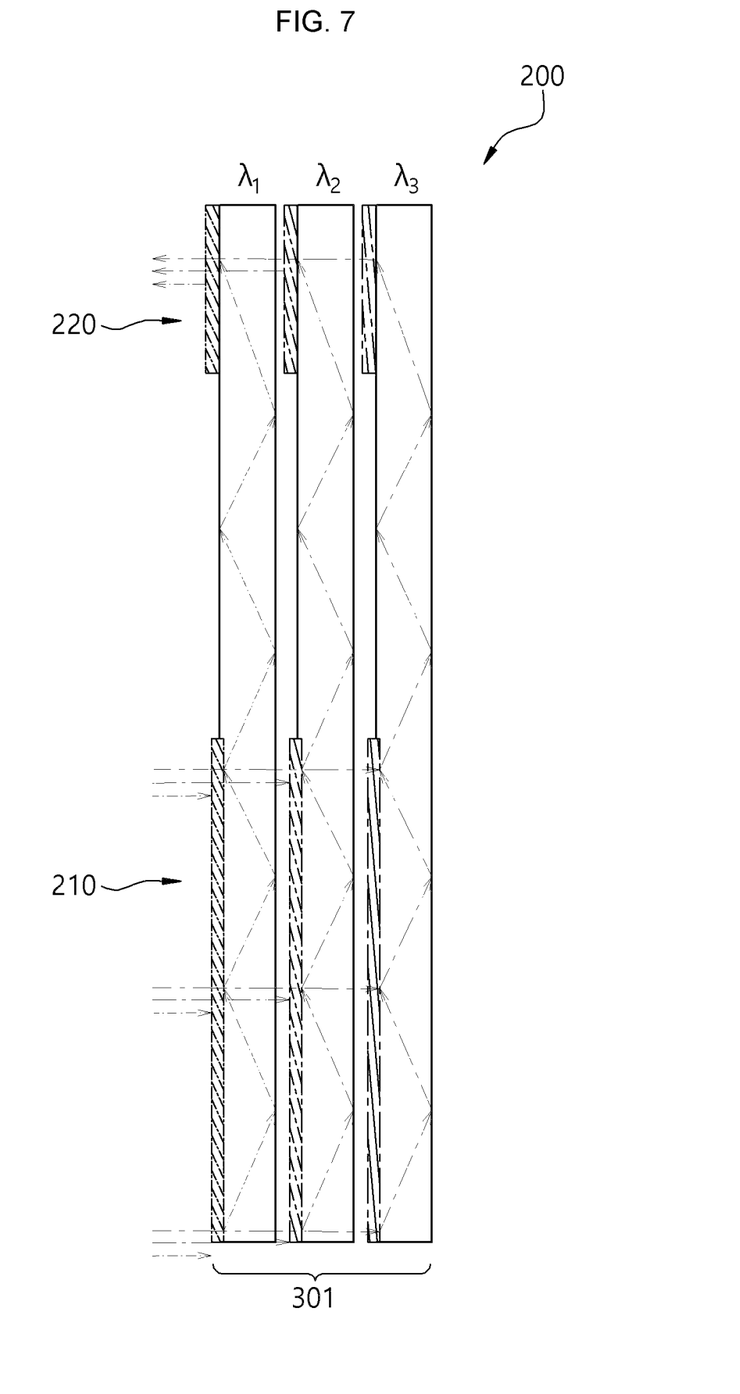
FIG. 7 is a conceptual diagram illustrating a first waveguide having three wavelength channels in FIGS. 5 and 6.

FIG. 7 illustrates a shape in which the first waveguide 301 has three wavelength channels.

Each of the three wavelength channels is a structure for solving chromatic aberration, is formed of a double-layer so as to allow a waveguide to be formed suitable for a specific wavelength, and fixes a diffraction angle or a refraction angle in each wavelength range to always be the same. Consequently, each wavelength may always be input to a first output coupler 220 at the same position.

Figure 8:
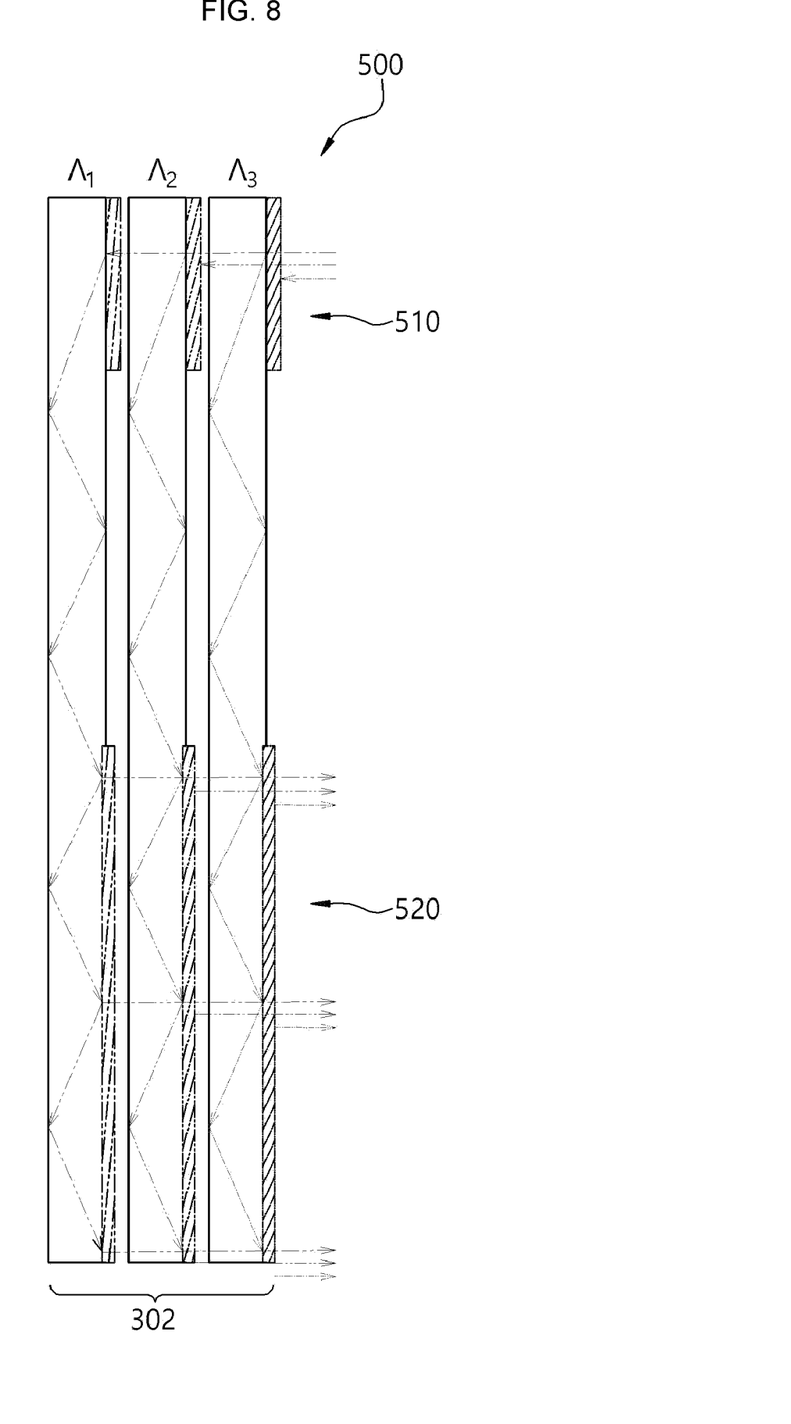
FIG. 8 is a conceptual diagram illustrating a second waveguide having three wavelength channels in FIGS. 5 and 6.

FIG. 8 illustrates a shape in which the second waveguide 302 has three wavelength channels.

Each of the three wavelength channels is a structure for solving chromatic aberration, is formed of a double-layer so as to allow a waveguide to be formed suitably for a specific wavelength, and fixes a diffraction angle or a refraction angle in each wavelength range to always be the same. Consequently, each wavelength may always be output at the same location.

As described above, in the augmented reality glasses 1 with auto coregistration of an invisible field on visible reality, the real space is directly recognized by the eyeball, and only near-infrared diagnosis and therapy information emitted from a specific area may be precisely coregistered to the real space so that, during surgery or a surgical procedure, there is a technical effect which is capable of showing the near-infrared rays with coregistration as augmented reality coaxially with the gaze of the clinician.

In accordance with augmented reality glasses with auto coregistration of an invisible field on visible reality according to the present invention, a real space can be directly recognized by an eyeball, and only near-infrared diagnosis and therapy information emitted from a specific area can be precisely coregistered to the real space so that, during surgery or a surgical procedure, there is a technical effect which is capable of showing the near-infrared rays with coregistration as augmented reality coaxially with the gaze of the clinician.

The descriptions of the above embodiments are provided to allow those skilled in the art to use or practice the present invention. Various modifications to these embodiments will be apparent to those skilled in the art, and the general principles defined herein can be applied to other embodiments without departing from the scope of the present invention. Thus, the present invention is not to be limited to the embodiments disclosed herein but is to be construed in the widest scope consistent with the principles or novel features disclosed herein.

What is claimed is:

1. Augmented reality glasses, comprising:
   a glasses body worn on a face of a user;
   an invisible light emission unit installed on one side of the glasses body and configured to emit invisible light toward a target object;
   an input unit installed on a front surface of the glasses body and configured to input the invisible light emitted from the target object together with visible light to a waveguide;
   an information processing unit installed on one side of the glasses body and configured to convert invisible light image information received from the input unit into visible light image information which is recognizable by a person; and
   an image output unit installed on a rear surface of the glasses body and configured to
      receive the visible light image information processed in the information processing unit, and
      output an image toward two eyeballs of the user through the waveguide based on the received visible light image information.

2. The augmented reality glasses of claim 1, further comprising:
   a focus adjustment unit installed on one side of the glasses body and configured to adjust a point at which gazes of the two eyeballs converge to exactly match a focus of real and augmented reality image information output from the image output unit; and an eyeball tracking unit installed on one side of the glasses body and configured to predict a vergence distance and transmit distance information to the focus adjustment unit.

3. The augmented reality glasses of claim 2, wherein:
the eyeball tracking unit tracks a gaze of the eyeball looking at a real space to determine the vergence distance and inputs determined information to the information processing unit; and
the information processing unit calculates the vergence distance of the eyeball in real time on the basis of input information.

4. The augmented reality glasses of claim 2, wherein the focus adjustment unit includes:
a first focus adjustment part formed as a transparent optical system, which includes one or more of a reflective element, a refractive element, a diffractive element, a holographic element, and a polarizing element, and causes refraction of light; and
a second focus adjustment part formed of a transparent optical system, which includes one or more of a reflective element, a refractive element, a diffractive element, a holographic element, and a polarizing element, and causes refraction of light.

5. The augmented reality glasses of claim 4, wherein the focus adjustment unit receives vergence distance information measured in the eyeball tracking unit and calculated in the information processing unit in real time, compares a focal length of a digital image including the invisible light information with the vergence distance of the eyeball, and maintains a difference between the focal length and the vergence distance within a diopter value of 0.25.

6. The augmented reality glasses of claim 4, wherein:
the first focus adjustment part is located on left and right sides to correspond to the two eyeballs of the user; and
the second focus adjustment part is located on the left and right sides to correspond to the two eyeballs of the user and formed to allow an image output position to be coregistered to gazes toward the target object.

7. The augmented reality glasses of claim 4, wherein the first focus adjustment part is formed to exhibit an effect equivalent to a depth of focus of an eyeball lens by acting in combination with a lens installed in a first output coupler of the input unit, thereby automatically applying a realistic optical blur to a camera of the input unit.

8. The augmented reality glasses of claim 4, wherein the second focus adjustment part increases or decreases a focal length by as much as a diopter value according to each user who needs vision correction.

9. The augmented reality glasses of claim 2, wherein the focus adjustment unit is formed in a parallel light structure in which a focus adjustment function of solving a vergence-accommodation conflict (VAC) problem is maintained and, simultaneously, a function of securing a quantity of light and implementing eye-box expansion through entrance pupil expansion and exit pupil expansion is achieved.

10. The augmented reality glasses of claim 2, wherein the eyeball tracking unit is formed of separate cameras and lighting which correspond to the two eyeballs or has a structure of a vergence tracker using electrooculographic signals of the two eyeballs.

11. The augmented reality glasses of claim 1, wherein the input unit includes:

a first input coupler which is formed in one end portion of the waveguide and on which invisible light is incident;
a first output coupler formed to be spaced a predetermined distance from the first input coupler in the other end portion of the waveguide and configured to output the invisible light incident from the first input coupler to a camera; and
the camera configured to capture the invisible light output from the first output coupler.

12. The augmented reality glasses of claim 11, wherein:
the camera transmits image information to the information processing unit; and
the information processing unit processes the received image information and transmits the processed image information to a display of the image output unit.

13. The augmented reality glasses of claim 11, wherein the image output unit includes:
a display configured to output the visible light image information received from the information processing unit;
a second input coupler formed in an end portion of the waveguide and configured to receive the visible light image information output from the display; and
a second output coupler installed to be spaced a predetermined distance from the second input coupler in the waveguide and formed to allow information received from the second input coupler to be output to the two eyeballs of a user,
wherein the second output coupler is formed to allow an image output position to correspond to an actual position of the target object, and each of the first input coupler, the first output coupler, the second input coupler, and the second output coupler secures a large viewing angle of 80 degrees or more by including and combining one or more of a reflective element, a refractive element, a diffractive element, a holographic element, and a polarizing element.

14. The augmented reality glasses of claim 13, wherein:
the first input coupler is located on each of left and right sides to correspond to the two eyeballs of the user;
the first output coupler and the camera are spaced apart from the first input coupler and located on the left and right sides in the glasses body;
the second output coupler is located on each of the left and right sides to correspond to the two eyeballs of the user; and
the display and the second input coupler are spaced apart from the second output coupler and located on the left and right sides in the glasses body,
wherein the second output coupler is formed to allow an image output position to be coregistered to gazes toward the target object.

15. The augmented reality glasses of claim 13, wherein each of the first input coupler and the second output coupler includes any one among a diffractive optical element, a holographic optical element, or a pin mirror.

16. The augmented reality glasses of claim 13, wherein a shape of each of the first output coupler and the second input coupler has a birdbath structure.

17. The augmented reality glasses of claim 11, wherein the first input coupler or the first output coupler further includes a filter on a front surface thereof to allow only the invisible light to be transmitted to the camera.

18. The augmented reality glasses of claim 1, wherein the image output unit includes:

a display configured to output the visible light image information received from the information processing unit;

a second input coupler formed in an end portion of the waveguide and configured to receive the visible light image information output from the display; and a second output coupler formed to be spaced a predetermined distance from the second input coupler in the waveguide and formed to allow information received from the second input coupler to be output to the two eyeballs of a user, wherein the second output coupler is formed to allow an image output position to correspond to an actual position of the target object.

19. The augmented reality glasses of claim 18, wherein the display transmits information included in the invisible light to the second input coupler in a form of visible light using a pseudo color which is contrasted with real image information recognized by the user.

20. The augmented reality glasses of claim 1, wherein the waveguide is formed of a first waveguide and a second waveguide, the first waveguide includes:

a first input coupler which is formed in one end portion of the first waveguide and on which the invisible light is incident;

a first output coupler formed to be spaced a predetermined distance from the first input coupler in the other end portion of the first waveguide and configured to output the invisible light incident from the first input coupler; and a camera configured to capture the invisible light output from the first output coupler, and the second waveguide includes:

a second input coupler formed in an end portion of the second waveguide and configured to receive image information output from a display of the image output unit; and a second output coupler installed to be spaced a predetermined distance from the second input coupler in the second waveguide and formed to allow information received from the second input coupler to be output to the two eyeballs of a user.

21. The augmented reality glasses of claim 20, wherein:

the first input coupler includes any one among a first diffractive optical element, a first holographic optical element, and a first pin mirror which are provided on one side of the first waveguide; and the second input coupler includes any one among a second diffractive optical element, a second holographic optical element, and a second pin mirror which are provided on one side of the second waveguide.

22. The augmented reality glasses of claim 20, wherein the first input coupler or the first output coupler further includes a first filter on a front surface thereof to allow only the invisible light to be transmitted to the camera.

23. The augmented reality glasses of claim 1, wherein the invisible light emission unit includes a second filter to allow only invisible light in a specific wavelength range to be emitted toward the target object.

24. The augmented reality glasses of claim 1, wherein:

the waveguide is made of a transparent optical material through which visible light passes;

any one among a freeform optical element, a flat optical device, and a curved optical device is used as the waveguide; and a vision correction function for the user is added to the waveguide as in ordinary glasses.

25. The augmented reality glasses of claim 1, wherein:

each of the input unit and the image output unit is formed in a structure having one or more wavelength channels; and the structure solves chromatic aberration by allowing only a specific wavelength to be transmitted to each of the one or more wavelength channels.

* * * * *